(12) United States Patent
Wechter et al.

(10) Patent No.: US 7,074,826 B2
(45) Date of Patent: Jul. 11, 2006

(54) R-NSAID ESTERS AND THEIR USE

(75) Inventors: William J. Wechter, Ojai, CA (US); Elaine Benaksas Schwartz, Yorba Linda, CA (US)

(73) Assignee: Encore Pharmaceuticals, Inc., Riverside, CA (US)

( * ) Notice: Subject to any disclaimer, the term of this patent is extended or adjusted under 35 U.S.C. 154(b) by 2 days.

(21) Appl. No.: 10/678,430

(22) Filed: Oct. 3, 2003

(65) Prior Publication Data

US 2004/0067914 A1    Apr. 8, 2004

Related U.S. Application Data

(60) Provisional application No. 60/416,980, filed on Oct. 7, 2002.

(51) Int. Cl.
*A61K 31/341* (2006.01)
*A61K 31/216* (2006.01)
*C07D 307/62* (2006.01)
*C07C 69/612* (2006.01)

(52) U.S. Cl. ............ 514/474; 549/317; 549/292; 546/238; 560/51; 560/56; 560/100; 560/102; 560/112; 514/532; 514/545; 514/544

(58) Field of Classification Search .......... 560/51, 560/56, 102, 100, 112; 514/532, 545, 474; 549/317, 292
See application file for complete search history.

(56) References Cited

U.S. PATENT DOCUMENTS 5,981,592 A * 11/1999 Wechter et al. ............ 514/570

2003/0027867 A1 * 2/2003 Zavitz

FOREIGN PATENT DOCUMENTS

EP    0 305 089 A1 *   3/1989

OTHER PUBLICATIONS

Wechter et al, Cancer Research, vol. 60, p. 2203-2208, Apr. 15, 2001.*
Kato, et al., Studies on Scavengers of Active Oxygen Species. 1. Synthesis and Biological Activity of 2-*O*-Alkylascorbic Acids, *J. Med. Chem.*, 31:793-798 (1988).
Manfredini, et al., Novel Antiosidant Agents Deriving From Molecular Combinations of Vitamins C and E Analogues: 3,4-Dihydroxy-5(*R*)-[2(*R,S*)-(6-hydroxy-2,5,7,8-tetramethylchroman-2(*R,S*)-yl-methyl)-[1,3]dioxolan-4(*S*)-yl]-5*H*-furan-2-one and 3-*O*-Octadecyl Deerivatives, *Bioorganic & Medical Chemistry*, 8:2791-2801 (2000).
Manfredini, et al., Design, Synthesis and Activity of Ascorbic Acid Prodrugs of Nipecotic, Kinurenic and Diclophenamic Acids, Liable to Increase Neurotropic Activity, *Journal of Medicinal Chemistry*, (Nov. 2001).

* cited by examiner

*Primary Examiner*—Bernard Dentz
(74) *Attorney, Agent, or Firm*—Hana Verny; Peters, Verny, Jones, Schmitt & Aston LLP (57) ABSTRACT

The present invention concerns esters of R-enantiomers of a non-steroidal anti-inflammatory drug, which is substantially free from the S-enantiomer. The compounds of the invention may be used in treating a disease or illness in a mammal. To this end, a composition comprising a compound mentioned above, or a pharmaceutically acceptable salt thereof where salt formation occurs, is administered to the mammal in an amount sufficient to elicit a chemopreventative effect or a chemoprotective effect or a therapeutic effect or a prophylactic effect.

30 Claims, 4 Drawing Sheets

FIG. 1

R-Flurbiprofen

R-Ketoprofen

R-Naproxen

R-Tiaprofen

R-Suprofen

R-Carprofen

R-Pirporfen

R-Indoprofen

R-Benoxaprofen

R-Ibuprofen

R-Ketorolac

R-Etodolac

*FIG. 2*

General Synthesis:

R-NSAID ESTERS AND THEIR USE

CROSS-REFERENCE TO RELATED APPLICATIONS

This application claims the benefit of the subject matter disclosed in prior copending Provisional Patent Application Ser. No. 60/416,980 filed Oct. 7, 2002, the disclosure of which is incorporated herein by reference in its entirety.

BACKGROUND OF THE INVENTION

This invention relates to various R-NSAID esters and their use in the treatment of illness and disease.

Neoplastic diseases are conditions in which abnormal proliferation of cells results in a mass of tissue called a neoplasm or tumor. Neoplasms have varying degrees of abnormalities in structure and behavior. Some neoplasms are benign while others are malignant or cancerous. An effective treatment of neoplastic disease would be considered a valuable contribution to the search for cancer preventive or curative procedures.

The gastrointestinal tract, including the rectum and colon, is lined with epithelial cells, which have a high proliferation rate. The lining of the colon, in particular, made up of columnar rows of epithelial cells, is characterized by a series of indentations or crypts. Epithelial cells in the bottom regions of the crypts proliferate and move upward toward the tops of the crypts. In the normal colon, the proliferation region of the large intestine normally occupies the basal or deeper three-quarters of the crypts. A relationship has been observed between the expansion of cell proliferation zones to the upper regions of the crypts and colon cancer. See M. Lipkin, "Biomarkers of Increased Susceptibility to Gastrointestinal Cancer: New Application to Studies of Cancer Prevention in Human Subjects,"Cancer Research, Vol. 48, pp. 235–245 (Jan. 15, 1988).

Cancer of the colon is common in the western world and is an important cause of morbidity and mortality, having an incidence of about 5% in the U.S. population. As with other types of cancers, cancers of the gastrointestinal tract, including colon cancer, are characterized by abnormal development in cell proliferation and differentiation in the gastrointestinal tract.

There has been an intensive search for chemopreventative agents for all individuals at risk for colon cancer and other gastrointestinal cancers, particularly individuals over the age of 45. One class of potentially therapeutically useful compounds is the non-steroidal anti-inflammatory drugs ("NSAIDs"). NSAID's, presently in common use as anti-inflammatory agents and as analgesics, are known to have neoplasia chemoprevention and other anti-neoplastic benefits. Physiologically, NSAID's are known to inhibit the biosynthesis of prostaglandins by the inhibition of the cyclooxygenase enzyme, which is ubiquitous in mammalian tissues. See Buckley et al., Drugs, 39(1):86–109 (1990). The role of NSAID's in prevention of colorectal cancer is discussed in Heath, et al., "Nonsteroidal Antiinflammatory Drugs and Human Cancer," Cancer, Vol. 74, No. 10, pp. 2885–2888 (Nov. 15, 1994).

However, the use of NSAID's in colon cancer prevention has been associated with severe undesirable side effects, which include gastrointestinal, renal and hepatic toxicities, as well as increases in bleeding times due to disruption of platelet function (e.g., thrombocytopenia), and prolongation of gestation due to uterine effects. Another serious side effect associated with the use of certain NSAID's is leukopenia (decreased white cell count in the blood), and consequent agranulocytosis.

Agranulocytosis is a life-threatening condition that develops very rapidly, and that is difficult to detect even with periodic white-cell counts. The leukopenia/agranulocytosis syndrome has been described for several NSAID's, such as indomethacin, ketoprofen, and ibuprofen. Indeed, such NSAID's are contraindicated in patients whose immune systems are compromised by HIV infection, chemotherapy, ionizing irradiation, corticosteroids, immunosuppressives, etc., or by such conditions as emphysema, bronchiectasis, diabetes mellitus, leukemia, burns and the like. A recent review of the adverse effects of NSAID's is Borda, et al., "NSAIDs: A Profile of Adverse Effects," Hanley and Belfus, Inc., Philadelphia, Pa., 1992.

The most recent epidemiologic survey showing that both aspirin and NSAID's confer protection against colon cancer is Peleg, et al., "Aspirin and Nonsteroidal Anti-inflammatory Drug Use and the Risk of Subsequent Colorectal Cancer," Arch. Intern. Med., Vol. 154, pp. 394–400 (Feb. 28, 1994). This reference identifies a causal relationship between the use of NSAID's, such as indomethacin, sulindac and peroxicam, and prevention of cancer of the large bowel and rectum. A risk benefit analysis is suggested, however, due to the severe potential gastrointestinal and renal side effects, particularly in the elderly.

The standard treatment for colon cancer currently consists of the administration of a known cancer-fighting agent, 5-fluorouracil in combination with the anthelmintic levamisole. No improvement in survival among colon cancer patients was shown when 5-fluorouracil was administered alone. The addition of levamisole, which is known to stimulate the immune system and increase T-cell count, showed improved survival rate among these patients. See Moertel, et al., "Levamisole and Fluorouracil for Adjuvant Therapy of Resected Colon Carcinoma," N Engl J Med 1990; 322:352–358.

Many NSAID's exhibit molecular chirality, and thus have R- and S-enantiomers. Such compounds typically are produced as racemic mixtures, which subsequently may be separated into the individual enantiomers.

The enantiomers of several 2-arylpropionic acid NSAID's are discussed in Yamaguchi, et al., Nippo Yakurigaku Zasshi, 90:295–302 (1987). Yamaguchi, et al. state that the S-enantiomers of 2-arylpropionic acids have 15–300 times higher prostaglandin synthetase inhibitory activities than the R-enantiomers in the rat. Caldwell, et al., Biochem. Pharmacol. 37: 105–114 (1988) allege that "at best, the R-isomers of 2-arylpropionic acids function as prodrugs for the therapeutically active S-forms" when the racemic drug is administered and, thus, add to both the therapeutic and toxic effects of the active S-enantiomers. Caldwell, et al. further contend that "at worst, the R-enantiomers are undesirable impurities in the active drug" causing difficulties due to non-stereoselective toxicity. The authors indicate that the use of the S-isomers alone should provide safer and more effective use of this class of drugs.

Similarly, it has been generalized that the pharmacokinetics of the enantiomers of 2-arylpropionic acids are different due, at least in part, to the unidirectional metabolic inversion of the R- to the S-enantiomer. However, it has been found that this interconversion depends on the particular compound and the particular species in which it is administered. Jamali, Eur. J. Drug Metabolism Pharmaco. 13: 1–9(1988).

Because of the toxicity and side effects previously described, many NSAID's are no longer in use in human medicine as analgesics. Some of these NSAID's include tiaprofenic acid, suprofen, carprofen, pirprofen and indoprofen.

A need has been identified for new formulations of NSAID's that are effective in treating neoplastic disease including colorectal and other cancers and are more tolerable with regard to gastrointestinal toxicity. Thus, it would be particularly desirable to provide compositions and methods for the prevention of neoplasia and colorectal cancer but without the aforementioned disadvantages.

Another disease for which effective treatment is needed is cystic fibrosis. Cystic fibrosis (CF) is a heritable disease that follows an autosomal recessive pattern of transmittance. It is the most common lethal genetic disease in the United States. The approximate frequency in Caucasians is 1 in 2000. Cystic fibrosis is characterized by abnormal eccrine and exocrine gland function. In particular, mucous glands produce viscous secretions that lead to chronic pulmonary disease, insufficient pancreatic and digestive function and abnormally concentrated sweat.

The most prominent theories of CF etiology focus on alterations in physiochemical properties of exocrine secretions, the regulation of exocrine gland secretions, electrolyte transport and abnormalities in serum. Typical presentations include early onset of respiratory symptoms such as colds, and recurrent respiratory infections later in life. CF patients show evidence of decreasing pulmonary function with time, and their sputum cultures often display *S. aureus, P. aeruginosa* and *P. capacia*.

The major source of CF morbidity is pulmonary disease. More than 98% of CF patients die of either respiratory failure or pulmonary complications. Antibiotics are the key element in increasing survival. Prior to the 1950's, when modern antibiotics began to become available, patients typically survived for only a few years. At present, the medial survival age is 24. Consequently, stimulation of neutrophil function as a means of clearing bacterial foci is thought to be an appropriate focus of treatment; however, the resulting inflammatory response can lead to other complications.

It has been reported (M. W. Konstan, et al., New England J. Med. 1995; 332:848–854) that high doses of racemic ibuprofen in cystic fibrosis patients over a four-year period slows progression of the lung disease. However, gastrointestinal side effects due to the presence of S(+)-ibuprofen severely limit the chronic use of this therapy, particularly at high dose and as the racemate (see Wechter, W. J. J. Clin. Pharmacol. 1994; 34:1036–1042 and Wechter et al. Chirality 1993; 5:492–494). It is believed that high doses of racemic ibuprofen inhibits the influx of neutrophils to the alveolar crevices, while low doses increase the influx of neutrophils. The high doses employed in the Konstan study also appear to cause conjunctivitis and epistaxis.

Still another disease for which effective treatment is needed is dementia including Alzheimer's Disease (AD), which is a degenerative brain disorder associated with extensive loss of specific neuronal subpopulations and characterized clinically by progressive loss of memory, cognition, reasoning, judgment and emotional stability that gradually leads to profound mental deterioration and ultimately death. AD is a common cause of progressive mental failure (dementia) in aged humans and is believed to represent the fourth most common medical cause of death in the United States. AD has been observed in varied races and ethnic groups worldwide and presents a major present and future public health problem. The disease is currently estimated to affect up to four million individuals in the United States alone. To date, AD has proven to be incurable, and presently causes up to 50,000 deaths yearly.

The brains of individuals with AD exhibit neuronal degeneration and characteristic lesions variously referred to as amyloidogenic plaques, vascular amyloid angiopathy, and neurofibrillary tangles. Large numbers of these lesions, particularly amyloidogenic plaques and neurofibrillary tangles, are generally found, in patients with AD, in several areas of the human brain important for memory and cognitive function. Smaller numbers of these lesions in a more restricted anatomical distribution are found in the brains of most aged humans who do not have clinical AD, as well as patients suffering from Down's Syndrome and Hereditary Cerebral Hemorrhage with Amyloidosis of the Dutch-Type.

It is presently believed that progressive cerebral deposition of particular amyloidogenic proteins, beta-amyloid proteins (beta AP), play a seminal role in the pathogenesis of AD and can precede cognitive symptoms by years or decades. Recently, it has been shown that beta AP are released from neuronal cells grown in culture and are present in cerebrospinal fluid (CSF) of both normal individuals and AD patients.

A possible correlation to the plaque pathology has been developed by several groups demonstrating the direct beta AP neurotoxicity toward cultured neurons. More recently, in addition to the direct neurotoxicity, an inflammatory response in the AD brain, perhaps elicited by beta AP, also contributes to the pathology of the disease. A limited clinical trial with the NSAID indomethacin exhibited a retardation in the progression of Alzheimer's dementia (Rogers, et al., Science, 266:1719–1720 (1993)).

Previous methods of treating AD are disclosed, for example, in U.S. Pat. No. 5,576,353 (use of N-propargyl-aminoindan compounds) and U.S. Pat. No. 5,552,415 (use of raloxifene and related compounds). A continuing need exists for effective methods for preventing, delaying, and treating AD.

Recently, a composition for use in preventing colorectal cancer and other neoplastic diseases, such as breast cancer was disclosed in U.S. Pat. Nos. 5,981,592 and 5,955,504. The composition includes an enantiomerically stable R-NSAID or a pharmaceutically acceptable salt thereof in an amount effective to elicit a chemopreventative effect. The composition is substantially free of the S-enantiomer of the R-NSAID. Therapeutic use of the composition is accompanied by reduced adverse side effects. A method of treating cystic fibrosis is also disclosed using the aforementioned composition. Furthermore, the composition was found useful in the treatment of Alzheimer's Disease.

A continuing need exists for compositions that are useful in the treatment of neoplastic disease, inflammation, cystic fibrosis, dementia, and the like. The compositions should allow for entry into tissue.

SUMMARY OF THE INVENTION

One embodiment of the present invention is a compound that is an ester of an R-enantiomer of a non-steroidal anti-inflammatory drug substantially free from the S-enantiomer wherein the esterifying agent comprises 3 to 6 carbon atoms, at least one hydroxyl group and optionally one or more carboxyl groups, 1 to 4 hydroxyl groups, one or more aldehyde groups, a gamma lactone, a delta lactone, an amine, an imine, a lactam and the like. The compounds of the invention may be used in treating a disease or illness in a mammal. To this end, a composition comprising an enantiomerically stable form of a compound mentioned above is administered to the mammal in an amount sufficient to elicit a chemoprotective effect or a therapeutic effect or a prophylactic effect.

Another embodiment of the present invention is a compound that is an ester of an R-enantiomer of a non-steroidal anti-inflammatory drug substantially free from the S-enantiomer wherein the esterifying agent is non-cyclic and comprises 3 to 6 carbon atoms, at least one hydroxyl group and optionally one or more carboxyl groups, 1 to 4 hydroxyl groups, one or more aldehyde groups, and the like.

Another embodiment of the present invention is a compound of the formula:

{Q-CH(A)-CH(D)-J-Q$^1$}-OC(O)W wherein, when not linked to —OC(O)W,
  A is OH, H, NH$_2$, a protecting group, or a group imparting a predetermined level of water solubility,
  D is OH, H, NH$_2$, a protecting group, or a group imparting water a predetermined level of solubility,
wherein J is C(G)=C(G), (CH(G))$_n$,
  n is 0, 1 or 2, and
wherein, when not linked to —OC(O)W,
  G is independently OH, H, NH$_2$, a protecting group, or a group imparting a predetermined level of water solubility,
wherein, when not a carbon linked to —OC(O)W,
  Q is H, CH—OH, CH$_3$, COOH or CHO,
  Q$^1$ is H, CH—OH, CH$_3$, COOH or CHO,
wherein, when Q$^1$ is COOH, n is 1 or 2, and A or D is OH, Q$^1$ may be taken together with A or D to form a lactone, and
wherein only one of A, D, G, Q or Q$^1$ comprises —OC(O)W, and
wherein W is an R-NSAID analog substantially free from S-enantiomer. Another embodiment of the present invention is a compound of the formula:

{Q-CH(A)-CH(D)-J-Q$^1$}-OC(O)W wherein, when not linked to —OC(O)W,
  A is OH, H, NH$_2$, a protecting group, or a group imparting a predetermined level of water solubility,
  D is OH, H, NH$_2$, a protecting group, or a group imparting water a predetermined level of solubility,
wherein J is C(G)=C(G), (CH(G))$_n$,
  n is 0, 1 or 2, and
  wherein, when not linked to —OC(O)W,
    G is independently OH, H, NH$_2$, a protecting group, or a group imparting a predetermined level of water solubility,
wherein, when not a carbon linked to —OC(O)W,
  Q is H, CH—OH, CH$_3$, COOH or CHO,
  Q$^1$ is H, CH—OH, CH$_3$, COOH or CHO,
wherein only one of A, D, G, Q or Q$^1$ comprises —OC(O)W, and
wherein W is an R-NSAID analog substantially free from S-enantiomer.

Another embodiment of the present invention is a compound of the formula:

{Q-CH(A)-CH(D)-J-Q$^1$}-OC(O)W wherein, when not linked to —OC(O)W,
  A is OH, H, NH$_2$, a protecting group, or a group imparting a predetermined level of water solubility,
  D is OH, H, NH$_2$, a protecting group, or a group imparting water a predetermined level of solubility,
wherein J is (CH(G))$_n$,
  n is 0, 1 or 2, and
  G is independently OH, H, NH$_2$, a protecting group, or a group imparting a predetermined level of water solubility,
wherein, when not a carbon linked to —OC(O)W,
  Q is H, CH—OH, CH$_3$, COOH or CHO,
  Q$^1$ is H, CH—OH, CH$_3$, COOH or CHO,
wherein only one of Q or A comprises —OC(O)W, and
wherein W is an R-NSAID analog substantially free from S-enantiomer.

Another embodiment of the present invention is a compound that is an ascorbic acid ester of an R-enantiomer of a non-steroidal anti-inflammatory drug substantially free from the S-enantiomer. The compounds of the invention may be used in treating a disease or illness in a mammal. To this end, a composition comprising an enantiomerically stable form of a compound mentioned above is administered to the mammal in an amount sufficient to elicit a chemoprotective effect or a therapeutic effect or a prophylactic effect.

Another embodiment of the present invention is a compound of Formula 1:

wherein Y is an R-NSAID analog substantially free from S-enantiomer,

X is H, a protecting group, a group imparting a predetermined level of water solubility and so forth.

Another embodiment of the present invention is a method for making a compound as mentioned above. The vicinal ring hydroxy groups of ascorbic acid are reacted with protecting groups. The terminal hydroxy group of the resultant ascorbic acid is reacted with an activated form of an R-NSAID and the protecting groups are removed to yield the above compound.

Another embodiment of the present invention includes compositions suitable for administration to a mammal having a disease-state, which composition comprises a therapeutically effective amount, or a chemopreventative amount, of the above compound.

Another embodiment of the present invention concerns a method for treating a mammal having a disease-state, which comprises administering a therapeutically effective amount, or a chemopreventative amount, of the above compound.

Other aspects of the invention relate to pharmaceutical compositions containing compounds of the above formulae in admixture with one or more pharmaceutically acceptable, non-toxic carriers.

DETAILED DESCRIPTION OF SPECIFIC EMBODIMENTS OF THE INVENTION

It has surprisingly been discovered that certain enantiomerically stable esters such as, for example, ascorbic acid esters, of R-isomers of NSAIDs, substantially free of the S-isomers, are highly effective in the treatment of various diseases and illnesses. Isomers are different compounds that have the same molecular formula. The aforementioned esters are more advantageous than their non-ester counterparts because the esters appear to be particularly facile at passing through the blood-brain barrier into the central nervous system. Furthermore, the administration of compositions including ascorbic acid esters of the R-isomers of NSAID's, which are substantially free of the S-enantiomer of the selected NSAID, is accompanied by a significant reduction in adverse effects associated with the administration of S-enantiomers or racemic mixtures of NSAID's. Such adverse effects include, but are not limited to, thrombocytopenia and consequent increases in bleeding times; leukopenia and agranulocytosis; prolongation of gestation; gastrointestinal toxicities such as gastric and intestinal ulcerations and erosions; renal toxicities such as papillary necrosis and chronic interstitial nephritis; and hepatic toxicities, such as jaundice, acute hepatitis and hepatic failure.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments and is not intended to be limiting. Instead, the scope of the present invention will be established by the appended claims.

Compounds of the Invention

In some embodiments, the inventive compositions comprise at least one enantiomerically stable ester of an R-isomer of an NSAID. The esterifying agent may comprise 3 to 6 carbon atoms, at least one hydroxyl group and optionally one or more carboxyl groups, 1 to 4 hydroxyl groups, one or more aldehyde groups, a gamma lactone, a delta lactone, an amine group, an imine group, a lactam and the like.

The terms "may" "optional" or "optionally" used herein sometimes interchangeably means that the subsequently described circumstance may or may not occur so that the description includes instances where the circumstance occurs and instances where it does not.

In some embodiments of the present invention, the compound is an ester of an R-enantiomer of a non-steroidal anti-inflammatory drug substantially free from the S-enantiomer wherein the esterifying agent is non-cyclic and comprises 3 to 6 carbon atoms, at least one hydroxyl group and optionally one or more carboxyl groups, 1 to 4 hydroxyl groups, one or more aldehyde groups, and the like. The term "non-cyclic" means that the esterifying agent does not comprise a ring structure.

In some embodiments the esterifying agent has the formula:

Q-CH(A)-CH(D)-J-Q¹ wherein A is OH, H, $NH_2$, a protecting group, or a group imparting a predetermined level of water solubility, D is OH, H, $NH_2$, a protecting group, or a group imparting water a predetermined level of solubility, wherein J is C(G)=C(G), $(CH(G))_n$ G is independently OH, H, $NH_2$, a protecting group, or a group imparting a predetermined level of water solubility, n is 0, 1 or 2,

Q is CH—OH, $CH_3$, COOH or CHO, $Q^1$ is H, CH—OH, $CH_3$, COOH or CHO, wherein, when $Q^1$ is COOH, n is 1 or 2, and A or D is OH, $Q^1$ may be taken together with A or D to form a lactone.

In some embodiments the esterifying agent has the formula:

Q-CH(A)-CH(D)-J-Q¹ wherein A is OH, H, $NH_2$, a protecting group, or a group imparting a predetermined level of water solubility, D is OH, H, $NH_2$, a protecting group, or a group imparting water a predetermined level of solubility, wherein J is C(G)=C(G), $(CH(G))_n$

G is independently OH, H, $NH_2$, a protecting group, or a group imparting a predetermined level of water solubility, n is 0, 1 or 2, Q is CH—OH, $CH_3$, COOH or CHO, $Q^1$ is H, CH—OH, $CH_3$, COOH or CHO.

In some embodiments the esterifying agent has the formula:

Q-CH(A)-CH(D)-J-Q¹ wherein A is OH, H, $NH_2$, a protecting group, or a group imparting a predetermined level of water solubility, D is OH, H, $NH_2$, a protecting group, or a group imparting water a predetermined level of solubility, wherein J is $(CH(G))_n$ G is independently OH, H, $NH_2$, a protecting group, or a group imparting a predetermined level of water solubility, n is 0, 1 or 2, Q is CH—OH, $CH_3$ or COOH, $Q^1$ is H, CH—OH, $CH_3$ or COOH.

Examples of esterifying agents include glycerol, propylene glycol, hydroxysuccinic acid, hydroxyglutamic acid, glyceric acid, tartaric acid, xylaric acid, malic acid, lactic acid, hydroxybutyric acid, ascorbic acid, and so forth and including derivatives, enantiomers, isomers, and so forth thereof. It should be understood that, for compounds not comprising a free hydroxyl group for ester formation, a hydroxyl derivative of such compound is employed.

The term "ascorbic acid" includes L-ascorbic acid and its enantiomer, D-erythorbic acid and its enantiomer, derivatives of the aforementioned including derivatives formed involving one or more of the free hydroxyl functionalities thereof including ethers, esters, ketones, and so forth, derivatives of the acid functionality including pharmaceutically acceptable salts thereof, esters, amides, amines, imines, and so forth, particularly, the aforementioned derivatives that include protecting groups, groups that impart a predetermined level of water solubility, and the like. By the phrase "predetermined level of water solubility" is meant that the level of water solubility of the resulting compound is such that the compound possesses a sufficient level of hydrophobicity to get across the blood-brain barrier.

The chemical structures of NSAID's vary. Certain NSAID's, such as ketoprofen and flurbiprofen are arylpropionic acids, while others are cyclized derivatives of arylpropionic acids, arylacetic acids, thiazinecarboxamides, etc. The R-NSAID's of the compounds of the invention are typically R-arylpropionic acids, cyclized derivatives of such acids and so forth that do not readily bioinvert to the S-enantiomer. By the phrase "do not readily invert to their S-enantiomers" is meant that less than 10%, less than 5%, less than 2% of the S-enantiomer is produced at doses specified herein, in order to preclude the side effects (or adverse effects) associated with the inhibition of COX-1 (cyclooxygenase-1) and COX-2 (cyclooxygenase-2) by the S-enantiomers. Depending on the structure of a particular NSAID, the compound exhibits chirality, i.e., has R- and S-enantiomers. In a typical embodiment, the NSAID employed in the compositions and methods claimed is an arylpropionic acid, in particular a compound selected from the group consisting of flurbiprofen, ketoprofen, naproxen, tiaprofenic acid, suprofen, carprofen, pirprofen, indoprofen, benoxaprofen, ibuprofen and the like. The NSAID can also be a cyclized derivative of arylpropionic acid, such as ketorolac, or an arylacetic acid, such as etodolac. All of these NSAID's have been used in human medicine in the U.S. and/or Europe as racemates, with the exception of naproxen, which is commercially available as the S-isomer only. Furthermore, the R-isomers of the above NSAID's have been shown to have utility in the treatment of certain diseases. See U.S. Pat. Nos. 6,160,018 and 5,955,504. It is a particularly attractive feature of the present invention that ascorbic acid esters of enantiomerically unstable propionic acid derivatives such as the R-isomer of ibuprofen may be used to treat disease and illness. According to U.S. Pat. No. 6,160,018, the R-isomers of such enantiomerically unstable propionic acid derivatives themselves are not suitable as treatment compositions.

Descriptions of specific NSAID's can be found in various publications. Ketoprofen, for example, is described in U.S. Pat. No. 3,641,127. A description of flurbiprofen is found in U.S. Pat. No. 3,755,427. Ketorolac, another chiral NSAID, is described in U.S. Pat. No. 4,089,969. A large number of NSAID's useful according to the invention is commercially available either in the form of racemic mixtures or as optically pure enantiomers. In all cases racemic mixtures contain equal amounts of the R- and S-isomers of the NSAID provided. For example, the following racemates can be obtained through Sigma Chemical Co.: ketoprofen, flurbiprofen, etodolac, suprofen, carprofen, indoprofen and benoxaprofen. Naproxen, marketed as the S-isomer only, is also available from this source. Additionally, many commercial sources exist for the stereospecific R-isomers of many NSAID's. R-ketoprofen, R-flurbiprofen and R-ketorolac, for example, are available through Sepracor, Inc.; R-naproxen can be obtained as the sodium salt through Sigma Chemical Co.; R-etodolac is available from Wyeth-Ayerst; R-tiaprofenic acid is available through Roussel (France, Canada, Switzerland, Spain, Denmark, Italy); R-suprofen is manufactured by McNiel Pharmaceuticals; R-carprofen is available from Roche; R-pirprofen is available through Ciba (France, Belgium, Denmark); R-indoprofen can be obtained through Carlo Elba (Italy, U.K.); and R-benoxaprofen is manufactured by Eli Lilly Co.

In addition to commercial sources, racemic mixtures of NSAID's, which are useful according to the invention, can be produced by methods described in numerous references and U.S. Patents. Synthesis of ketoprofen, for example, is described in U.S. Pat. No. 3,641,127, which is hereby incorporated by reference, while the synthesis of racemic ketorolac is disclosed in Muchowski, et al., J. Med. Chem., 28(8):1037–1049 (1985). The optically pure R-isomers of the selected NSAID's can then be obtained by resolving the racemic mixtures according to well-known methods. See, e.g., U.S. Pat. No. 5,331,000 (R-ketoprofen) and U.S. Pat. No. 5,382,591 (R-ketorolac), the disclosures of each of which are incorporated herein by reference.

As mentioned above, the ascorbic acid esters of the R-NSAID's are enantiomerically stable. As used herein, the term "enantiomerically stable" means that at steady state there is no more than about 20% of the circulating NSAID as its S-enantiomer and typically no more than 10% (i.e., 90% R, 10% S). A suitable measure of this ratio is obtained by evaluating the relative concentrations of the two enantiomers in the blood plasma or urine vs. time. The rate of change of enantiomer concentration in plasma, for example, is assumed to reflect quantitatively the change in drug concentrations throughout the body. This rate can be approximated by first-order kinetics. See Gibaldi, et al., Pharmacokinetics, (1982) Chapter 1, pp. 1–5, which is incorporated herein by reference.

Pharmacokinetic data and an explanation of the present state of knowledge for many NSAID's are presented in Jamali, "Pharmacokinetics of Enantiomers of Chiral Non-steroidal Anti-inflammatory Drugs," Eur. J Drug Metab. Pharmacokin. (1988), Vol. 13, No. 1, pp. 1–9, which is incorporated herein by reference.

The term "substantially free" of the S-isomer indicates that the amount of S-isomer of the NSAID, if any, present in the composition is insufficient to elicit an adverse effect in the patient to whom the composition is administered or, at most elicits an adverse effect that is tolerable to the patient and is outweighed by the beneficial effect or effects. Usually, the inventive composition contains no more than about 10% by weight of the corresponding S-isomer of the NSAID, based upon the total amount of NSAID present in the composition. Typically, the inventive composition contains no more than about 5% by weight of the corresponding S-isomer of the NSAID. More typically, the inventive composition contains no more than about 1% of the corresponding S-isomer of the NSAID.

In some embodiments of the present invention, the compound has the formula:

wherein, when not linked to —OC(O)W,
    A is OH, H, NH$_2$, a protecting group, or a group imparting a predetermined level of water solubility,
    D is OH, H, NH$_2$, a protecting group, or a group imparting water a predetermined level of solubility, wherein J is C(G)=C(G), (CH(G))$_n$,
    n is 0, 1 or 2, and wherein, when not linked to —OC(O)W,
    G is independently OH, H, NH$_2$, a protecting group, or a group imparting a predetermined level of water solubility, wherein, when not a carbon linked to —OC(O)W, Q is H, CH—OH, CH$_3$, COOH or CHO, Q$^1$ is H, CH—OH, CH$_3$, COOH or CHO, wherein, when Q$^1$ is COOH, n is 1 or 2, and A or D is OH, Q$^1$ may be taken together with A or D to form a lactone, and wherein only one of A, D, G, Q or Q$^1$ comprises —OC(O)W, and wherein W is an R-NSAID analog substantially free from S-enantiomer.

In some embodiments of the present invention, the compound has the formula:

{Q-CH(A)-CH(D)-J-Q$^1$}-OC(O)W wherein, when not linked to —OC(O)W,

A is OH, H, NH$_2$, a protecting group, or a group imparting a predetermined level of water solubility, D is OH, H, NH$_2$, a protecting group, or a group imparting water a predetermined level of solubility, wherein J is C(G)=C(G), (CH(G))$_n$, n is 0, 1 or 2, and wherein, when not linked to —OC(O)W, G is independently OH, H, NH$_2$, a protecting group, or a group imparting a predetermined level of water solubility, wherein, when not a carbon linked to —OC(O)W, Q is H, CH—OH, CH$_3$, COOH or CHO, Q$^1$ is H, CH—OH, CH$_3$, COOH or CHO, wherein only one of A, D, G, Q or Q$^1$ comprises —OC(O)W, and wherein W is an R-NSAID analog substantially free from S-enantiomer.

In some embodiments of the present invention, the compound has the formula:

{Q-CH(A)-CH(D)-J-Q$^1$}-OC(O)W wherein, when not linked to —OC(O)W,

A is OH, H, NH$_2$, a protecting group, or a group imparting a predetermined level of water solubility, D is OH, H, NH$_2$, a protecting group, or a group imparting water a predetermined level of solubility, wherein J is (CH(G))$_n$, n is 0, 1 or 2, and G is independently OH, H, NH$_2$, a protecting group, or a group imparting a predetermined level of water solubility, Q$^1$ is H, CH—OH, CH$_3$ COOH, wherein, when not a carbon linked to —OC(O)W,

Q is H, C—OC(O)W, CH—OH, CH$_3$ or COOH, wherein only one of Q or A comprises —OC(O)W, and wherein W is an R-NSAID analog substantially free from S-enantiomer.

Some embodiments of compounds in accordance with the present invention have the following formula (Formula 1):

wherein Y is an R-NSAID analog substantially free from S-enantiomer,

X is H, a protecting group as described more fully below, a group imparting water solubility and so forth.

A group imparting water solubility is a hydrophilic functionality, which increases wettability of solids with water and the solubility in water of compounds to which it is bound. Such functional group or functionality can be a substituent having 1 to 50 or more atoms and can include a group having a sulfonate, sulfate, phosphate, amidine, phosphonate, carboxylate, hydroxyl particularly polyols such as polyglycol ether alcohol, amine such as polyamine, ether, amide, and the like. Illustrative functional groups are carboxyalkyl, sulfonoxyalkyl, CONHOCH$_2$COOH, CO-(glucosamine), sugars, dextran, cyclodextrin, SO$_2$NHCH$_2$COOH, SO$_3$H, CONHCH$_2$CH$_2$SO$_3$H, PO$_3$H$_2$, OPO$_3$H$_2$, hydroxyl, carboxyl, ketone, and combinations thereof. Also included within the scope of the invention are pharmaceutically acceptable salts of any of the above groups that permit salt formation such as, e.g., phosphate salts, sulfonate salts, and the like.

Also included within the scope of the compounds of the present invention are pharmaceutically acceptable salts of the esters of the R-isomer of an NSAID where the nature of the NSAID and/or the esterifying agent permits salt formation. For example, etodolac, carprofen, ketorolac, piprofen, indoprofen and benoxaprofen all contain a nitrogen atom, which form a pharmaceutically acceptable salt. A pharmaceutically acceptable salt refers to those salts which retain the biological effectiveness and properties of the original molecule and which are not biologically or otherwise undesirable. For the nitrogen containing NSAID's the salts are usually acid addition salts formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. For the esterifying agent that comprises a carboxyl group such as, for example, succinic acid, glutamic acid, tartaric acid, malic acid, ascorbic acid, and so forth, the salts are usually trimethyl ammonium, sodium, potassium, etc.

Methods of Preparation, Isolation and Purification of the Compounds Preparation

Figure 3:
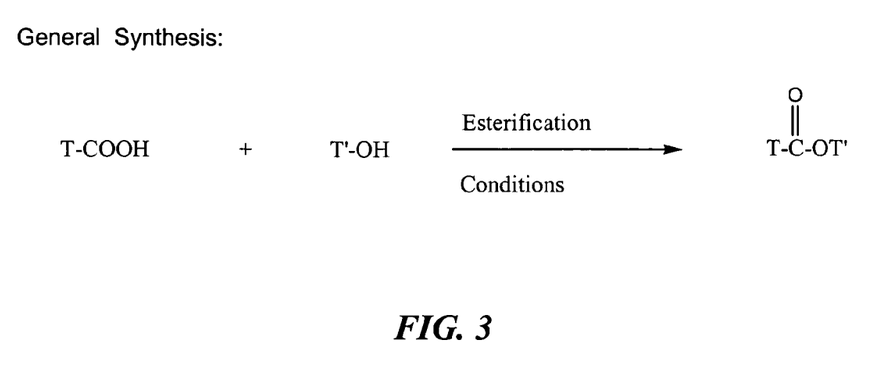
FIG. 3 is a general scheme for preparing esters of the present invention.

In general, compounds of the invention may be prepared by protecting hydroxyl (or alcohol) groups on the esterifying agent other than the hydroxyl group that is to be condensed with the carboxylic acid group of the R-NSAID to form the ester thereof. The ester is generally formed in the presence of a condensation agent as is known in the art. An exemplary embodiment of the synthesis is set forth in FIG. 3. Referring to FIG. 3, an R-NSAID (T-COOH) is combined with the esterifying agent (T'-OH) under Esterification Conditions, which usually include an activation agent such as, for example, N,N,-dicyclohexylcarbodiimide (DCC) and the like, in a suitable solvent such as, for example, an aromatic amine, e.g., pyridine, N,N-dimethylaminopyridine, etc., and so forth. The activation agent may be bound to a polymer. See, for example, Bull. Chem. Soc. Japan, 54, 631 (1981). A more detailed discussion of the above is set forth below.

Figure 4:
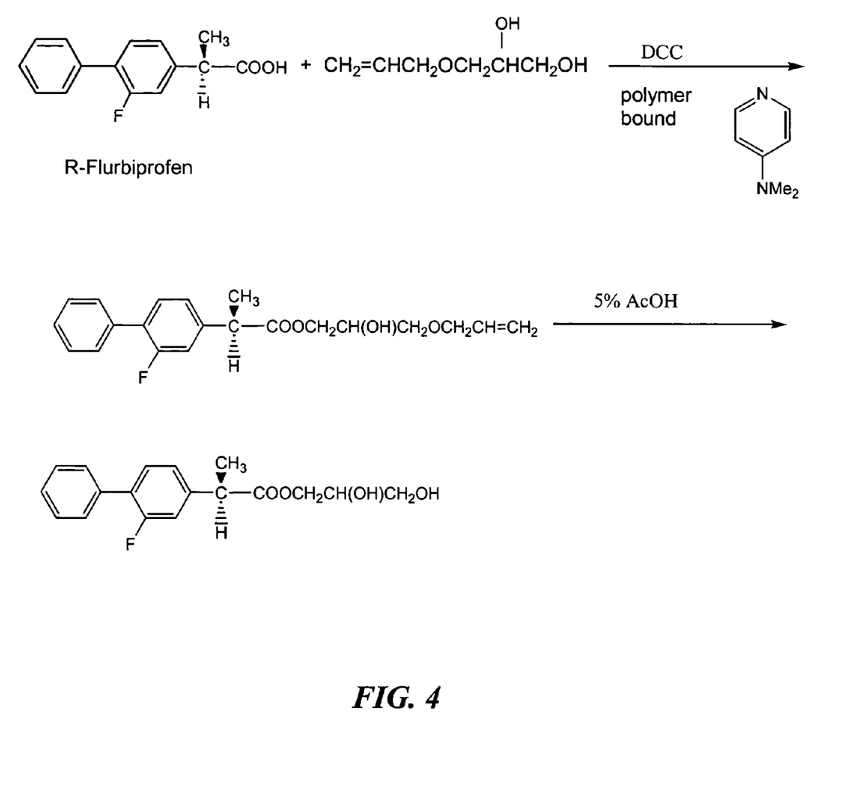
FIG. 4 is a scheme for the synthesis of a glycerol ester of an R-NSAID.

A particular embodiment of a preparation of a compound in accordance with the present invention is depicted in FIG. 4. A glycerol ester of the R-NSAID flurbiprofen is formed. R-flurbiprofen is combined with allyl glycerol (commercially available protected form of glycerol) in the presence of polymer bound DCC in N,N-dimethylaminopyridine to form the ester derivative. The resulting compound is treated with dilute acetic acid (5% AcOH) to remove the allyl protecting group and give the glycerol ester of R-flurbiprofen.

As indicated above, the preparation of the compounds of the invention may involve protecting terminal or primary hydroxyl groups as well as any other hydroxyl groups on the esterifying agent other than the hydroxyl group involved in the ester formation. Protection relates to the addition of chemical protecting groups using conventional materials and techniques within the skill of the art and/or described in detail in numerous patents and articles in the technical literature; for example, reference can be made to Greene, et al., Protective Groups in Organic Synthesis, $2^{nd}$ Ed., New York, John Wiley & Sons (1991). Protecting groups prevent the site to which they are attached from participating in the chemical reaction to be carried out. The particular protecting group chosen depends on the nature of the reaction to be performed and the conditions of such reaction such as temperature, pH, and so forth. Examples of such protecting groups, by way of example and not limitation, are trimethylsilyl-, 2-methoxyethoxymethyl-, 4-chlorophenyl chloroformate (in pyridine), bromobenzyloxy, carbamyl, formyl, allyl, t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyloxycarbonyl, alpha-dimethyl-3,5-dimethoxybenxyloxycarbonyl, o-nitrophenylsulfenyl, 2-cyano-1,1-dimentylethoxycarbonyl, and the like. The reaction is usually carried out in a buffered medium under basic conditions. The reaction is carried out at a temperature of about 0° C. to 50° C., typically, 0° C. to 30° C., for a period of about 0.1 to about 24 hours, typically, 0.3 to 10 hours, usually under an inert gas such as nitrogen, argon and the like. The medium may be an organic solvent such as pyridine, an ether, e.g., THF, etc., and the like. The reaction may require basic conditions such as, for example, a metal hydride, e.g., sodium hydride, an alkyl amine, e.g., ethyl amine, etc., a suitable carbonate such as potassium carbonate, sodium carbonate, and the like. One of the above reagents may be included in the reaction medium to provide for basic conditions where such conditions are desired.

One or more hydroxyl groups may be protected with a different protecting group than the other hydroxyl groups. In this way, the protecting group on one or more of the hydroxy groups, particularly a terminal or primary hydroxyl group, may be removed without removing the other protecting groups. Suitable protecting groups for the terminal hydroxyl group include trimethylsilyl and the like. The protected esterifying agent is treated under conditions that remove the protecting group on the terminal or primary hydroxyl group and not the other protecting groups. Such conditions are determined primarily by the nature of the protecting group and are known to those skilled in the art. For example, where trimethylsilyl protecting group is employed, the resulting fully protected molecule may be treated with fluoride, e.g., tetrabutylamine fluoride, in an ether solvent, e.g., THF, at a temperature of about 0° C. to 50° C., typically, 0° C. to 30° C., for a period of about 30 minutes to about 2 hours.

Next, the free hydroxy group of the resultant esterifying agent is reacted with an activated form of an R-NSAID. To this end, the R-NSAID is treated to convert the carboxylic acid to an activated form that can subsequently react with the terminal hydroxy group of the protected a scorbic acid. In one approach the carboxylic acid functionality is activated to permit an acylation reaction between the activated carboxylic acid group of the R-NSAID and the terminal hydroxy of the protected ascorbic acid. The carboxylic acid functionality of the R-NSAID may be converted to an acid halide such as an acid chloride, an acid bromide and so forth. "Halide" denotes fluoride, chloride, bromide, or iodide. Such conversions are well known in the art. See, for example, R. Nakao, et al., Bull. Chem. Soc. Jpn., 54, 1267 (1981).

In addition, carboxylic compounds may be activated to form esters with N-hydroxysuccinimide or its sulfo-analog, or to mixed anhydrides through reaction with carbitol chloroformate or t-butylchloroformate, or may be coupled directly using carbodiimides such as EDAC. The reaction conditions depend on the nature of the activation and so forth. The reaction is carried out at a temperature of about 0° C. to 50° C., typically, about 10° C. to about 30° C., for a period of about 15 minutes to about 120 hours, typically, about 30 minutes to about 100 hours, usually under an inert gas such as nitrogen, argon and the like. The medium may be an organic solvent such as pyridine, dimethylaminopyridine, an ether, e.g., THF, etc., and the like.

Following formation of the ester, the protecting groups are removed to yield the desired compound. Removal of the protecting groups is dependent on the nature of the protecting group. Suitable procedures are well known in the art. See, for example, Greene, et al., Protective Groups in Organic Synthesis, $2^{nd}$ Ed., New York, John Wiley & Sons (1991).

The solvents employed in the above synthetic procedures are usually inert solvents, i.e., a solvent inert under the conditions of the reaction being described in conjunction therewith, including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, dioxane, pyridine, substituted pyridines and the like.

Figure 1:
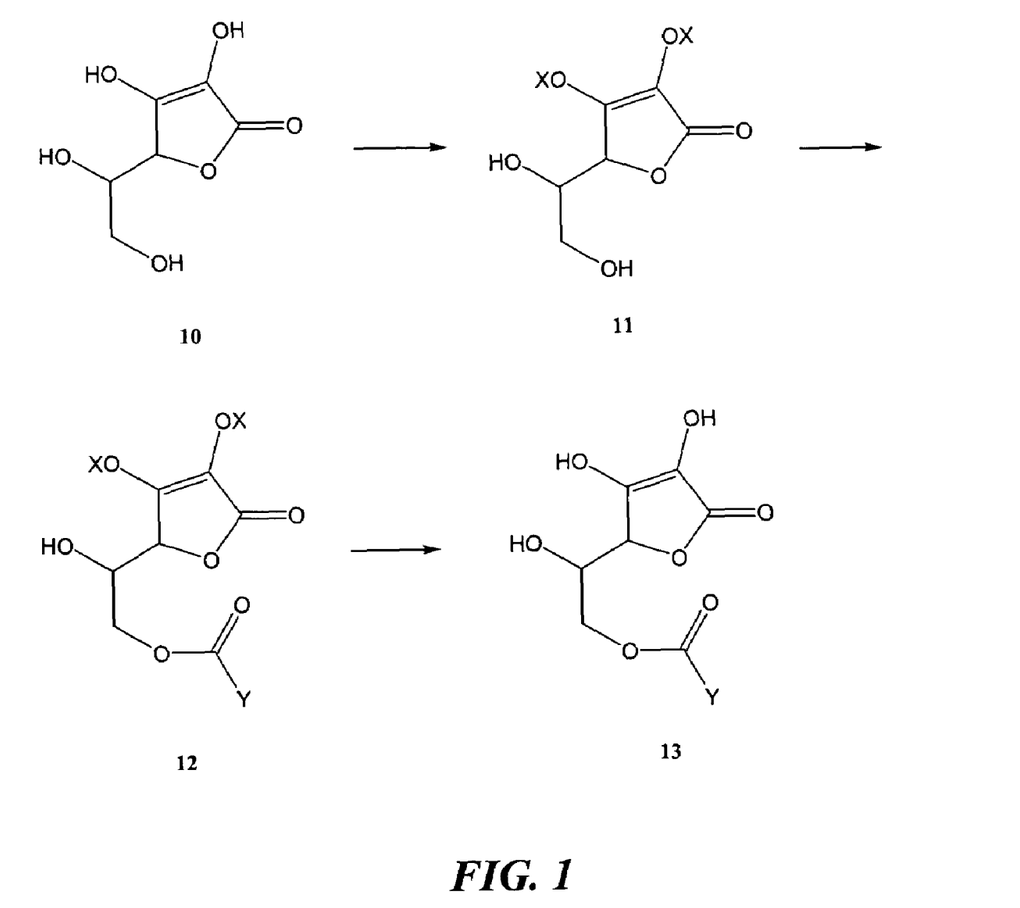
FIG. 1 is as chematic depicting an example of a reaction scheme for the preparation of compounds in accordance with the present invention.

An exemplary synthesis of an activated ester of an R-isomer of an NSAID is depicted in FIG. 1 by way of illustration and not limitation. The vicinal hydroxy groups of ascorbic acid 10 are reacted with protecting groups X to give compound 11. Subsequent reaction of compound 11 with an activated R-isomer of an NSAID, having the carboxylic acid group of the NSAID activated to form the acid chloride, yields compound 12. The protecting groups are removed to give compound 13, namely, an ascorbic acid ester of the R-isomer of an NSAID.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-performance liquid chromatography or a combination of these procedures. Specific illustrations of suitable separation and isolation procedures can be had by reference to the Examples hereinbelow. However, other equivalent separation or isolation procedures could, of course, also be used.

Utility, Testing and Administration:

Utility

The compounds of formula 1 and the pharmaceutically acceptable acid addition salts thereof are found to possess valuable pharmacological properties. The compounds of the invention may be used in treating a disease or illness in a mammal, for example, a human. To this end, a composition comprising an enantiomerically stable form of a compound mentioned above is administered to the mammal in an amount sufficient to effect treatment of the mammal. Such treatment may include eliciting a chemoprotective effect or a therapeutic effect or a prophylactic effect.

Disease states that are alleviated by treatment with a compound in accordance include, by way of illustration and not limitation, inflammation, cystic fibrosis, dementia, neoplastic disease, periodontal disease, and so forth. Dementia includes Alzheimer's disease, Parkinson's disease, Huntington's disease, and so forth. Neoplastic disease includes cancers such as, for example, adenocarcinomas, for instance, gastrointestinal cancers including colon cancer, rectal cancer, breast cancer, and the like.

Effective to elicit a therapeutic effect means that an overall improvement in the disease state or the illness state is achieved and includes relieving the disease or illness, i.e. causing regression of the disease or illness. A therapeutically effective amount refers to that amount which is sufficient to effect treatment, as defined above, when administered to a mammal in need of such treatment. The therapeutically effective amount will vary depending on the subject and disease state or illness state being treated, the severity of the affliction and the manner of administration, and may be determined routinely by one of ordinary skill in the art. In general the human dose may be about 1 to 2000 mg per 70 kilogram of body weight administered once or twice a day. Ideally, the dose is the lowest dose associated with activity and lack of other medical events.

Effective to elicit a chemopreventative effect means that abnormal cell proliferation is reduced. A method of measuring cell proliferation in animals is the Labeling Index (LI). Epithelial cells of the distal colon are stained using a histologic biomarker of proliferating cells. Microscopic examination allows for quantification of the proportion of proliferating cells in the crypts. A high proportion of proliferating cells or LI, particularly in the upper portion of the crypts, is an indicator of abnormal cell proliferation. A reduction in the LI of at least 10 to 50%, typically, at least 30% is associated with the reduction of abnormal cell proliferation. Of course, the particular R-NSAID used must be enantiomerically stable in the animal species being tested.

Chemoprevention in man and animals can also be measured by the inhibition of the conversion of the intestinal polyps, in an animal prone to polyposis, to neoplastic or cancerous legions. A min/+ mouse model can also be used to measure chemopreventive effect. Chemoprevention is achieved in this model if administration of the R-NSAID retards the spontaneous production of intestinal tumors in a min/+ mouse. Another test of chemoprevention is demonstrated by the prevention of induced tumors in a carcinogen treated mouse or rat.

Effective to elicit a prophylactic effect includes preventing the disease or illness from occurring in a subject that may be predisposed to the disease but has not yet been diagnosed as having it, inhibiting the disease or illness, i.e. arresting its development, in an early stage of disease, for example, the dysplastic stages of epithelial cancers, high PIN in prostate cancer, BRACA 1 and 2 mutations in women for the prevention of breast cancer, colon polyps in colon cancer, MRI or PET detected lesions or high A-beta proteins in the blood or CSF of patients with potential dementias. Alternatively, this treatment, which is cytostatic, usually can be used for "secondary chemoprevention" after cytoreduction therapy of a neoplastic disease by surgery or conventional cancer therapy.

Chemoprotective agents protect healthy tissue from the toxic effects of anticancer drugs.

Testing

Potential for a specific activity may be determined in vitro and in vivo by methods that are known in the art using the compounds of the invention such as, for example, A-beta protein ratios in blood or CSF.

Administration

The pharmaceutical compositions of the present invention comprise an ester such as, for example, a glycerol ester, a propylene glycol ester, an ascorbic acid ester, and the like, of the R-isomer of an NSAID as the active ingredient and may also contain a pharmaceutically acceptable carrier, and optionally, other therapeutic ingredients. The active ingredient may be a pharmaceutically acceptable salt of the ascorbic acid ester of the R-isomer of an NSAID where the nature of the NSAID permits salt formation.

"Optional" or "optionally" means that the subsequently described event or circumstance may or may not occur, and that the description includes instances where said event or circumstance occurs and instances in which it does not. For example, "optionally, other therapeutic agents" means that another therapeutic agent may or may not be present in the composition.

In applying the compounds of this invention to treatment of the above condition, administration of the active compounds and salts described herein can be by means of any of the accepted modes of administration for similar pharmaceutical compositions including oral, intravenous, rectal, parenteral (subcutaneous, intramuscular, intravenous), and like forms of administration, intrathecal, transdermal and other systemic routes of administration, and so forth. Any pharmaceutically acceptable mode of administration can be used, including solid, semi-solid or liquid dosage forms, such as, for example, tablets, troches, suppositories, pills, capsules, powders, liquids, dispersions, suspensions, solutions, elixirs, aerosols, patches and the like, typically in unit dosage forms suitable for single administration of precise dosages, or in sustained or controlled release dosage forms for the prolonged administration of the compound at a predetermined rate. It is noteworthy for the present invention that modes and routes of administration other than intrathecal are effective in the administration of the compounds to an individual in need thereof.

In addition to the common forms set out above, the compounds of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference in their entireties.

The amount of active compound administered will, of course, be dependent on the subject being treated, the severity of the affliction, the manner of administration and the judgment of the prescribing physician. In general, the amount of the compound administered is that which is sufficient to bring about the desired therapeutic effect or a chemoprotective effect or a prophylactic effect. An effective dosage is usually in the range of from about 1.0 mg to about 2000 mg per day in one or more doses. In one approach, the composition was administered in an amount of from about 10 mg to about 800 mg once or twice a day.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the conventional methods of pharmacy, but all methods include the step of bringing into association the active ingredient with the carrier, which constitutes one or more necessary ingredients.

The compositions will typically include a conventional pharmaceutical carrier or excipient and an active compound of the invention or the pharmaceutically acceptable salts thereof and, in addition, may include other medicinal agents, pharmaceutical agents, carriers, adjuvants, etc. Carriers such as starches, sugars, microcrystalline cellulose, diluents, granulating agents, lubricants, binders, disintegrating agents, and the like may be used in the cases of oral solid preparations. Oral solid preparations (such as powders, capsules, and tablets) are preferred over oral liquid preparations. The most preferred oral solid preparations are tablets. If desired, tablets may be coated by standard aqueous or non-aqueous techniques.

In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet contains from about 1 mg to about 1000 mg of the active ingredient, and each cachet or capsule contains from about 1 mg to about 600 mg of the active ingredient. Most typically, the tablet, cachet or capsule contains either one of four dosages, about 1 mg, about 50 mg, about 100 mg and about 200 mg of the active ingredient.

For solid compositions, conventional non-toxic solid carriers include, for example, pharmaceutical grades of mannitol, lactose, starch, magnesium stearate, sodium saccharin, talcum, cellulose, sodium crosscarmellose, glucose, sucrose, magnesium carbonate, and the like. The active compound as defined above may be formulated as suppositories using, for example, polyalkylene glycols, for example, propylene glycol, as the carrier. Liquid pharmaceutically administratable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition or formulation to be administered will, in any event, contain a quantity of the active compound(s) in an amount effective to alleviate the symptoms or their onset of the subject being treated.

Dosage forms or compositions containing active ingredient that is an ascorbic acid ester of the R-isomer of an NSAID (or a salt where permitted) in the range of 0.025 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, sodium crosscarmellose, glucose, sucrose, magnesium, carbonate, and the like. Such compositions take the form of solutions, suspensions, tablets, capsules, powders, sustained release formulations and the like. Such compositions may contain 0.1%–95% active ingredient, typically 0.5–80%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is hereby incorporated by reference.

The percentage of active compound contained in such parental compositions is highly dependent on the specific nature thereof, as well as the activity of the compound and the needs of the subject. However, percentages of active ingredient of 0.01% to 10% in solution are employable, and will be higher if the composition is a solid, which will be subsequently diluted to the above percentages. Typically, the composition will comprise 0.02–8% of the active agent in solution.

For systemic administration via suppository, traditional binders and carriers include, e.g. polyalkylene glycols or triglycerides. Such suppositories may be formed from mixtures containing active ingredient in the range of 0.05%–10%, typically 0.1–2%.

In order to aid in patient compliance with daily dosage requirements, the ascorbic acid esters of R-isomers of NSAID's may also be administered by formulating them in a toothpaste. The drug is dissolved in an ethyl alcohol solution and added to the toothpaste so that the final concentration of the active ingredient is from about 0.01 to about 1% on a weight compositions of the present invention basis.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see *Remington's Pharmaceutical Sciences*, Mack Publishing Company, Easton, Pa., 16th Edition, 1980.

Specific Utilities

The magnitude of a prophylactic or therapeutic dose of an ascorbic acid ester of an R-isomer of an NSAID in the acute or chronic management of cancer or neoplastic disease will vary with the particular NSAID, the severity of the condition to be treated, and the route of administration. The dose and/or the dose frequency also vary according to the age, body weight, and response of the individual patient.

In general and as mentioned above, the total daily dose range for a compound of the invention, for the conditions described herein, is from about 1 mg to about 2000 mg per 70 kilogram of body weight, in single or divided doses. Typically, a daily dose range for cancer prevention should be between about 1 mg to about 500 mg in single or divided doses. The typical daily dose for treatment of neoplastic disease should be about 1.0 mg to about 2000 mg in single or divided doses.

In managing the patient, the therapy should be initiated at a lower dose, perhaps about 1 mg to about 100 mg and increased up to about 1000 mg or higher depending on the patient's global response. It is further recommended that infants, children, patients over 65 years, and those with impaired renal or hepatic function, initially receive low doses, and that they be titrated based on individual response (s) and blood level(s).

It may be necessary to use dosages outside these ranges in some cases as will be apparent to those skilled in the art. Further, it is noted that the ordinary skilled clinician or treating physician will know how and when to interrupt, adjust or terminate therapy in consideration of individual patient response.

The present method of treatment of colorectal cancer will be enhanced by the use of an ascorbic acid ester of an R-isomer of an NSAID as an adjuvant to known chemotherapeutic agents such as 5-fluorouracil and the like.

The present compounds act with reduced gastrointestinal toxicity, which means that the administration of the particular compound of the invention is less ulcerogenic to the gastrointestinal tract of the human or other mammal than the corresponding racemate or S-isomer of the NSAID. One measure of ulcerogenic activity is the small bowel ulcer score. A rat is treated daily through oral administration of the ascorbic acid ester of an R-isomer of an NSAID for 30 days. At the end of the 30 days, the rat is sacrificed and the intestines removed. Lesions of appreciable size in the mucosa are measured. A cumulative score equaling the sum of the diameters of the ulcers measured are reported as the ulcer score. An ulcer score essentially equal to that of a control rat, or a reduction of the ulcer score of at least 50 to 90%, typically at least 80%, as compared to the corresponding S-NSAID or racemate, is considered a reduction in gastrointestinal toxicity.

In accordance with the present invention, cystic fibrosis patients are treated with an ascorbic acid ester of an R-isomer of an NSAID at high dose, that is, at an effective cystic fibrosis therapeutic amount. As used herein, an "effective cystic fibrosis therapeutic amount" is an amount that relieves CF symptoms, which can be measured by improved pulmonary function. More specifically, an effective cystic fibrosis therapeutic amount will be within the range from about 200 to 2000 mg per kilogram of body weight of a compound of the invention, the amount being typically administered in a divided dose based on the plasma half-life of the particular compound.

Additionally, administration of an ascorbic acid ester of an R-isomer of an NSAID appears to prevent or delay the onset of Alzheimer's Disease, without the attendant COX-mediated toxicity. Thus, in accordance with the present invention, patients at risk of developing Alzheimer's Disease patients are treated with an ascorbic acid ester of an R-isomer of an NSAID at high dose, that is, at an effective Alzheimer's Disease prophylactic amount. As used herein, an "effective Alzheimer's Disease prophylactic amount" is that amount which will delay the onset of symptoms of AD by at least 6 months. More specifically, an effective AD prophylactic amount will be within the range from about 50 to 2000 mg of the selected R-NSAID per day, the amount again being typically administered in a divided dose based on the plasma half-life of the particular R-NSAID.

Specific Embodiments of Compounds in Accordance with the Present Invention

Figure 2:
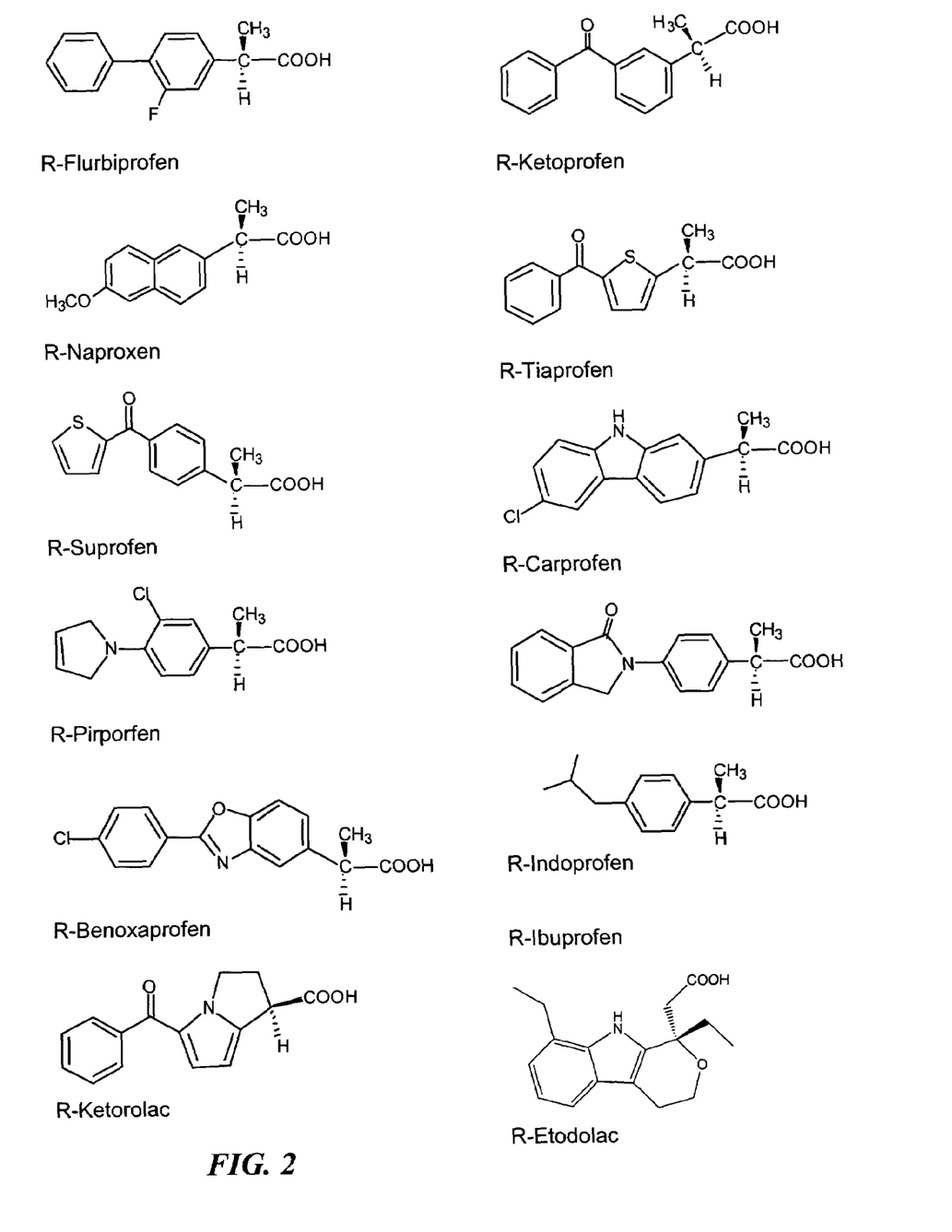
FIG. 2 depicts exemplary R-NSAID compounds that may be employed to form ascorbic acid esters in accordance with the present invention.

One series of compounds in accordance with the present invention includes compounds represented by Formula 2.

wherein Y is an R-NSAID analog substantially free from S-enantiomer, wherein the R-NSAID analog is the R-NSAID without the COOH group and the R-NSAID is selected from the group consisting of the compounds depicted in FIG. 2.

The invention is further illustrated by reference to the following examples describing the preparation of some of the compositions of the present invention, as well as their utility. It will be apparent to those skilled in the art that many modifications, both to materials and methods, may be practiced without departing from the purpose and interest of this invention.

EXAMPLES

The invention is demonstrated further by the following illustrative examples. Parts and percentages are by weight unless otherwise specified. Temperatures are in degrees Centigrade unless specified otherwise. The following preparations and examples illustrate the invention but are not intended to limit its scope.

Example 1

Preparation of a Compound of the Invention

The terminal or primary hydroxyl group of ascorbic acid is first protected as a trimethylsilyl ether. Accordingly, the ascorbic acid is reacted with trimethylsilyl chloride in the presence of triethylamine in tetrahydrofuran as the solvent for a period of 8 hours at a temperature of 25° C. The three remaining hydroxyl on the ascorbic acid are protected with 2-methoxyethoxymethyl ether (MEM). To this end the trimethylsilyl product from above is treated with MEM Cl in the presence of sodium hydride in tetrahydrofuran for a period of 1 hour at a temperature of 0° C. The trimethylsilyl ether group is removed to give free primary hydroxyl group by treatment with tetra-butyl ammonium fluoride in tetrahydrofuran for a period of 1 hour at a temperature of 25° C. The free primary hydroxyl group is reacted with the R-NSAID carboxylic acid group to form MEM protected ascorbic acid R-NSAID ester. The product from above with free primary hydroxyl group is combined with the R-NSAID in methyltetrahydrofuran in the presence of triethylamine for a period of up to 100 hours at a temperature of 25° C. The remaining protecting groups (MEM) are removed by treatment of the above product with titanium tetrachloride in methylene chloride for a period of 20 minutes at a temperature of 25° C. to give the R-NSAID ester of ascorbic acid.

Example 2

Composition for Oral Administration

| The composition contains: | % wt./wt. |
|---|---|
| Active ingredient | 20% |
| Lactose | 79.5% |
| Magnesium stearate | 0.5% |

The two ingredients are mixed and dispensed into capsules containing 100 mg each; one capsule would approximate a total daily dosage.

Example 3

Composition for Oral Administration

| The composition contains: | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The above ingredients are combined and granulated using alcohol as solvent. The formulation is then dried and formed into tablets (containing 20 mg of active compound) with an appropriate tableting machine.

Example 4

Parenteral Formulation (IV)

| The composition contains: | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 5

Suppository Formulation

| The composition contains: | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 6

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

Example 7

Toothpaste Formulation

| Ingredients | % wt./wt. |
|---|---|
| Active compound | 1 |
| 70% Sorbitol | 30 |
| Water | 25 |
| Glycerin | 18 |
| Dental Silica | 23 |
| Carboxymethlycellulose (CMC) | 0.9 |
| Sodium lauryl sulfate (SLS) | 0.75 |
| Flavor | 0.5 |

-continued

| Ingredients | % wt./wt. |
|---|---|
| Titanium Dioxide | 0.4 |
| Sodium Saccharin | 0.25 |
| Sodium Benzoate | 0.1 |
| Color | 0.003 |

Active ingredient is mixed with a portion of glycerin, the CMC is mixed with a portion of glycerin, the SLS is mixed with a portion of sorbitol. These are added sequentially to a mixture of all other ingredients, except flavor, and mixed after each addition. The flavor is added and mixed. The mixture is filled into squeezable tubes.

In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs.

All patents and other references cited in this application, are incorporated into this application by reference except insofar as they may conflict with those of the present application (in which case the present application prevails).

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A compound that is an ester of an R-enantiomer of a non-steroidal anti-inflammatory drug substantially free from the S-enantiomer wherein the alcohol part of said ester is from an esterifying agent comprising 3 to 6 carbon atoms, at least one hydroxyl group and in addition at least one group independently selected from one or more carboxyl groups, 1 to 4 hydroxyl groups, one or more aldehyde groups, a gamma lactone, a delta lactone, an amine, an imine or a lactam and wherein said non-steroidal anti-inflammatory is an arylpropionic acid or a cyclized derivative thereof.

2. A compound according to claim 1 wherein said esterifying agent has the formula:

$$Q\text{-CH(A)-CH(D)-J-}Q^1$$

wherein A is OH, H, $NH_2$, a protecting group, or a group imparting a predetermined level of water solubility,
D is OH, H, $NH_2$, a protecting group, or a group imparting water a predetermined level of a solubility,
wherein J is $C(G)=C(G)$, $(CH(G))_n$
G is independently OH, H, $NH_2$, a protecting group, or a group imparting a predetermined level of water solubility,
n is 0, 1 or 2,
Q is CH—OH, $CH_3$, COOH or CHO,
$Q^1$ is H, CH—OH, $CH_3$, COOH or CHO,
wherein, when $Q^1$ is COOH, n is 1 or 2, and A or D is OH, $Q^1$ may be taken together with A or D to form a lactone.

3. A compound according to claim 1 wherein said esterifying agent has the formula:

$$Q\text{-CH(A)-CH(D)-J-}Q^1$$

wherein A is OH, H, $NH_2$, a protecting group, or a group imparting a predetermined level of water solubility,
D is OH, H, $NH_2$, a protecting group, or a group imparting water a predetermined level of solubility,
wherein J is $C(G)=C(G)$, $(CH(G))_n$
G is independently OH, H, $NH_2$, a protecting group, or a group imparting a predetermined level of water solubility,
n is 0, 1 or 2,
Q is CH—OH, $CH_3$, COOH or CHO,
$Q^1$ is H, CH—OH, $CH_3$, COOH or CHO.

4. A compound according to claim 1 wherein said esterifying agent has the formula:

$$Q\text{-CH(A)-CH(D)-J-}Q^1$$

wherein A is OH, H, $NH_2$, a protecting group, or a group imparting a predetermined level of water solubility,
D is OH, H, $NH_2$, a protecting group, or a group imparting water a predetermined level of solubility,
wherein J is $(CH(G))^n$
G is independently OH, H, $NH_2$, a protecting group, or a group imparting a predetermined level of water solubility,
n is 0, 1 or 2,
Q is CH—OH, $CH_3$ or COOH,
$Q^1$ is H, CH—OH, $CH_3$ or COOH.

5. A compound according to claim 1 wherein said esterifying agent is selected from the group consisting of ascorbic acid, glycerol, propylene glycol, hydroxysuccinic acid, hydroxyglutamic acid, glyceric acid, tartaric acid, xylaric acid, malic acid, lactic acid and hydroxybutyric acid.

6. A compound according to claim 1 wherein said non-steroidal anti-inflammatory drug is selected from the group consisting of naproxen, flurbiprofen, ibuprofen, etodolac, ketoprofen, ketorolac, tiaprofenic acid, suprofen, carprofen, pirprofen, indoprofen, and benoxaprofen.

7. A compound that is an ester of an R-enantiomer of a non-steroidal anti-inflammatory drug substantially free from the S-enantiomer wherein the alcohol part of said ester is from an esterifying agent that is non-cyclic and comprises 3 to 6 carbon atoms, at least one hydroxyl group and in addition at least one group independently selected from one or more carboxyl groups and 1 to 4 hydroxyl groups and wherein said non-steroidal anti-inflammatory is an arylpropionic acid or a cyclized derivative thereof.

8. A compound according to claim 7 wherein said esterifying agent is selected from the group consisting of glycerol, propylene glycol, hydroxysuccinic acid, hydroxyglutamic acid, glyceric acid, tartaric acid, xylaric acid, malic acid, lactic acid and hydroxybutyric acid.

9. A compound according to claim 7 wherein said non-steroidal anti-inflammatory drug is selected from the group consisting of naproxen, flurbiprofen, ibuprofen, etodolac, ketoprofen, ketorolac, tiaprofenic acid, suprofen, carprofen, pirprofen, indoprofen, and benoxaprofen.

10. A compound of the formula:

wherein, when not linked to —OC(O)W,
A is OH, H, $NH_2$, a protecting group, or a group imparting a predetermined level of water solubility,
D is OH, H, $NH_2$, a protecting group, or a group imparting water a predetermined level of solubility,
wherein J is C(G)=C(G), $(CH(G))_n$,
n is 0, 1 or 2, and
wherein, when not linked to —OC(O)W,
G is independently OH, H, $NH_2$, a protecting group, or a group imparting a predetermined level of water solubility,
wherein, when not a carbon linked to —OC(O)W,
Q is H, CH—OH, $CH_3$, COOH or CHO,
$Q^1$ is H, CH—OH, $CH_3$, COOH or CHO,
wherein, when $Q^1$ is COOH, n is 1 or 2, and A or D is OH, $Q^1$ may be taken together with A or D to form a lactone, and wherein only one of A, D, G, Q or $Q^1$ comprises —OC(O)W, and
wherein W is an R-NSAID analog substantially free from S-enantiomer and wherein said R-NSAID is an arylpropionic acid or a cyclized derivative thereof and wherein said compound comprises one or more carboxyl groups and 1 to 4 hydroxyl groups.

11. A compound according to claim 10 wherein said non-steroidal anti-inflammatory drug is selected from the group consisting of naproxen, flurbiprofen, ibuprofen, etodolac, ketoprofen, ketorolac, tiaprofenic acid, suprofen, carprofen, pirprofen, indoprofen, and benoxaprofen.

12. A compound, which is an ascorbic acid ester of an R-enantiomer of a non-steroidal anti-inflammatory drug substantially free from the S-enantiomer, or a pharmaceutically acceptable salt thereof and wherein said non-steroidal anti-inflammatory is an arylpropionic acid or a cyclized derivative thereof.

13. A compound according to claim 12 wherein said non-steroidal anti-inflammatory drug is selected from the group consisting of naproxen, flurbiprofen, ibuprofen, etodolac, ketoprofen, ketorolac, tiaprofenic acid, suprofen, carprofen, pirprofen, indoprofen, and benoxaprofen.

14. A compound according to claim 13 wherein said ascorbic acid is selected from the group consisting of L-ascorbic acid and its enantiomer and D-erythorbic acid and its enantiomer.

15. A method for treating a disease or illness in a mammal wherein said disease or illness is inflammation, cystic fibrosis, Alzheimer's disease or neoplastic disease, said method comprising administering to said mammal a composition comprising an enantiomerically stable form of a compound according to claim 1 in an amount effective to elicit a chemopreventative effect or a therapeutic effect or a prophylactic effect or a chemoprotective effect.

16. A method according to claim 15 wherein said mammal is a human.

17. A method according to claim 15 wherein said composition is administered orally, transdermally, intravenously or by suppository.

18. A method according to claim 15 wherein said composition is administered in an amount of from about 1.0 mg to about 2000 mg per day in one or more doses.

19. A method according to claim 15 wherein said composition is administered in an amount of from about 10 mg to about 800 mg once or twice a day.

20. A method according to claim 15 wherein said composition comprises a pharmaceutically acceptable carrier.

21. A compound of the formula:

wherein Y is an R-NSAID analog substantially free from S-enantiomer and wherein said non-steroidal anti-inflammatory is an arylpropionic acid or a cyclized derivative thereof,
X is H, a protecting group, or a group imparting a predetermined level of water solubility,
or a pharmaceutically acceptable salt thereof.

22. A compound according to claim 21 wherein said R-NSAID analog is selected from the group consisting of analogs of R-naproxen, R-flurbiprofen, R-ibuprofen, R-etodolac, R-ketoprofen, R-ketorolac, R-tiaprofenic acid, R-suprofen, R-carprofen, R-pirprofen, R-indoprofen, and R-benoxaprofen.

23. A method for treating a disease or illness in a mammal wherein said disease or illness is inflammation, cystic fibrosis, Alzheimer's disease or neoplastic disease, said method comprising administering to said mammal a composition comprising an enantiomerically stable form of a compound according to claim 21 in an amount effective to elicit a chemoprotective effect or therapeutic effect.

24. A method according to claim 23 wherein said mammal is a human.

25. A method according to claim 20 wherein said composition is administered orally, transdermally, intravenously or intrathecally.

26. A method according to claim 23 wherein said composition is administered in an amount of from about 1.0 mg to about 2000 mg per day in one or more doses.

27. A method according to claim 23 wherein said composition is administered in an amount of from about 10 mg to about 800 mg once or twice a day.

28. A method according to claim 23 wherein said composition comprises a pharmaceutically acceptable carrier.

29. A method for making a compound of claim 12, said method comprising:
(a) reacting the terminal hydroxy group of said ascorbic acid with a protecting group,
(b) reacting the vicinal ring hydroxy groups and the secondary hydroxy group of said ascorbic acid with protecting groups,
(c) removing the protecting group from the terminal hydroxy group and reacting the terminal hydroxy group of said ascorbic acid with an activated form of said R-NSAID and
(d) removing said protecting groups.

30. A method according to claim 29 wherein said NSAID comprises a nitrogen atom and said method further comprises preparing an acid addition salt thereof.

* * * * *